United States Patent [19]

Kubler et al.

[11] Patent Number: 5,009,106
[45] Date of Patent: Apr. 23, 1991

[54] ACCELEROMETER WITH IMPROVED SHOCK RESISTANCE

[75] Inventors: John M. Kubler, Amherst; Michael D. Insalaco, Niagara Falls, both of N.Y.

[73] Assignee: Kistler Instrumente AG, Winterthur, Switzerland

[21] Appl. No.: 376,010

[22] Filed: Jul. 6, 1989

[51] Int. Cl.[5] .............................................. G01P 15/09
[52] U.S. Cl. ...................................... 73/651; 310/329; 310/348
[58] Field of Search ...................... 73/517 R, 526, 651; 310/329, 348

[56] References Cited

U.S. PATENT DOCUMENTS

| 3,673,441 | 6/1972 | Royster | 310/348 |
| 4,337,641 | 7/1982 | Sugihara et al. | 310/329 |
| 4,373,378 | 2/1983 | Fujishiro et al. | 73/651 |

FOREIGN PATENT DOCUMENTS 747008  1/1944  Fed. Rep. of Germany ...... 310/329

OTHER PUBLICATIONS

*Modal Testing, Theory and Practice*, by D. E. Ewins, Research Study Press Ltd., 1984, pp. 87–152.

Primary Examiner—John Chapman
Attorney, Agent, or Firm—Barnes & Thornburg

[57] ABSTRACT

The shock resistance of an accelerometer for the measurement of an axial acceleration, having a sensing part consisting of an electromechanical beam, a spacer and a beam carrier can significantly be improved by making the two sections of the oscillating beam of unequal lengths and by providing the beam with a length between 8 mm and 11 mm and a width between 2.5 mm and 6.5 mm at a thickness of 0.6 mm. That way an optimum relationship between measuring sensitivity and shock resistance of the accelerometer will be reached.

5 Claims, 3 Drawing Sheets $l1 > l2$

ACCELEROMETER WITH IMPROVED SHOCK RESISTANCE

BACKGROUND AND SUMMARY OF THE INVENTION

The invention relates generally to an accelerometer for the measurement of an axial acceleration, with sensing part consisting of an electromechanical beam, a spacer and a beam carrier and more specifically to a shock resistant accelerometer.

The knowledge of the vibrating behavior of technical structures has recently, because of its significance, obtained a special name, namely "Modal testing". The purpose of the analysis consists in creating a mathematical model of the vibrating behavior of a structure. Accelerations, as they occur for instance in connection with vibrations, are measured with accelerometers. In many cases the measurement of axial accelerations is sufficient, and it is possible to neglect the angular accelerations. The measurement of axial acceleration is achieved by fastening the accelerometer at the surface of the object to be measured, either by screwing or by gluing. An accelerometer already introduced in practice has a sensing part consisting of a pair of electromechanical sections of beam with equal dimensions, arranged symmetrically to a main axis, a spacer and a beam carrier. The spacer is situated in this main axis and is connected with the sections of the beam at one end and with the beam carrier at the other end. The beam carrier lies on two opposite steps of the housing and is solidly fixed. Thus the sensing part, consisting of the two sections of the beam, the spacer and the beam carrier, is formed as a suspension construction. Accelerometers for the measurement of an axial acceleration of this kind are already commercially available.

The theory of "Modal testing" is described for instance in the book "Modal Testing, Theory and Practice", by D. E. Ewins, Research Study Press Ltd., 1984, on pages 87–152.

An important disadvantage of the already commercially available accelerometers is the fragility of the sensing part. By mounting or dismounting a measuring instrument, it is often dropped on the floor and the sensible sensing part breaks.

Thus it is an object of the invention to create an accelerometer with improved shock resistance. According to the invention, this objective is reached by making the two sections of the beam of unequal length. Furthermore the shock resistance can be improved by appropriate dimensions of the beam and convenient fastening of the spacer at the beam.

Other objects, advantages and novel features of the present invention will become apparent from the following detailed description of the invention when considered in conjuction with the accompanying drawings.

DETAILED DESCRIPTION OF THE DRAWINGS

Figure 1:
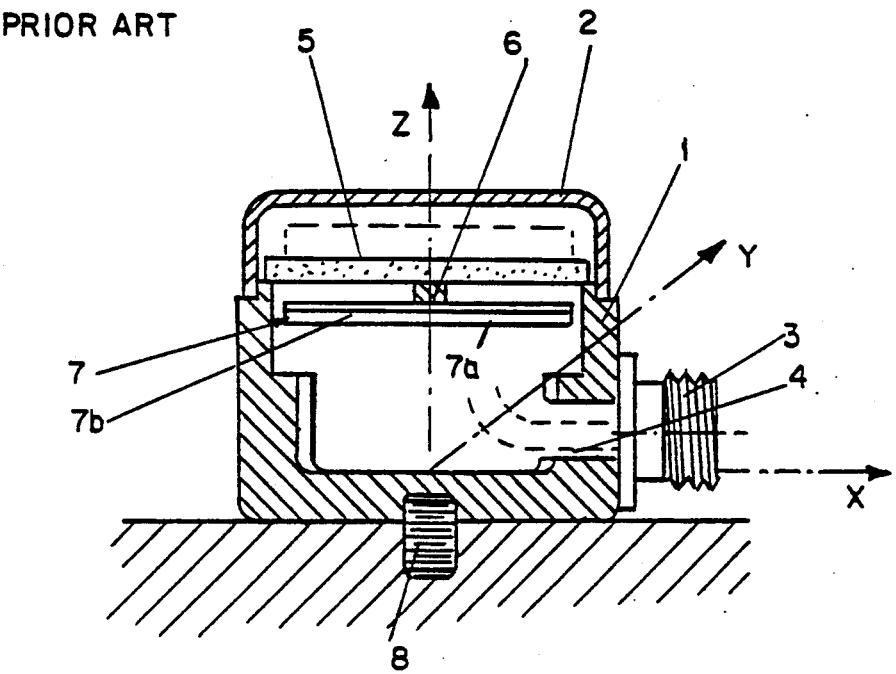
FIG. 1 is a cross-sectional view of an accelerometer with beam of the prior art.

FIG. 1 shows a cross section through an accelerometer for the measurement of the axial acceleration as used for Modal analysis according to the prior art. The working principle has been described above. A housing 1, closed by a cover 2, contains a sensing part consisting of an beam 7, a spacer 6 and a beam carrier 5. The housing 1 is fastened at the surface of the object to be measured by a screw 8. Therefore it follows the vibrations of the object, which will be transferred to the beam carrier 5 across the spacer 6, and, finally to the beam 7, which transforms them to electrical signals (piezo electirc of Bimorph-element). These signals are transmitted to a plug contact 3 via signal transmitting cables 4. The accelerometer described above processes only signals coming from vibrations in the Z-direction. The spacer 6 supports the beam in its central axis (main axis of the system, Z). By measuring the amplitude of this system as a function of the frequency w, the broken curve "a" representing A$\omega$ of FIG. 3 will result.

Figure 2:
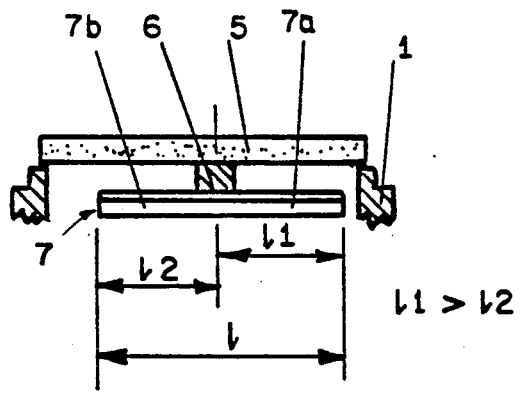
FIG. 2 is a cross-sectional view of the sensing part of an accelerometer according to the invention.
Figure 3:
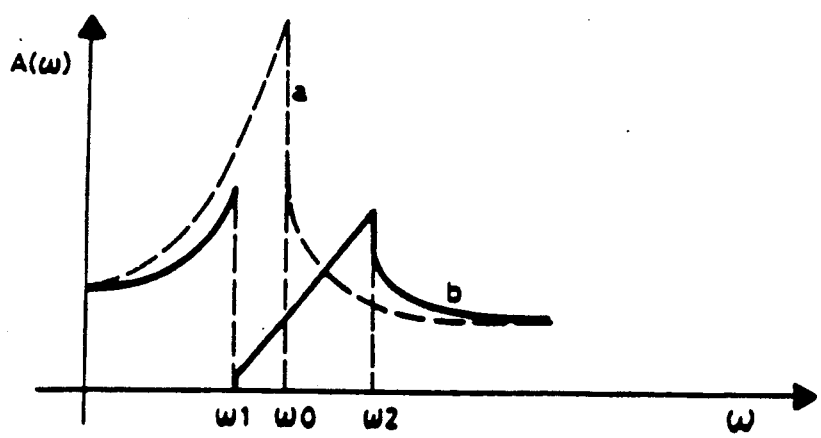
FIG. 3 is a graph of the amplitude A $\omega$ as function of the oscillating frequency w; wherein curve a, in broken line is: centrical supporting of the oscillating beam; and curve b, in unbroken line is: eccentrical supporting of the beam.

FIG. 2 shows a cross section through the sensing part 5, 6, 7 of an accelerometer according to the invention. The numbers have the same significance as in FIG. 1. The difference to the prior art represented by FIG. 1 consists in the different supporting area. The beam is not centrically supported, but is eccentrically supported. The beam 7 still consists of a bar of the length 1, but is technically divided into two sections 7a and 7b of the different lengths $l_1$ and $l_2$. Each of these beam sections has its own natural frequency. FIG. 3 shows also the resonance curve A$\omega$ of this oscillating system as curve "b" (unbroken line). One recognizes two natural frequencies $\omega_1$ and $\omega_2$, the lower one ($\omega_1$) being related to the longer beam section $l_1$, the higher one ($\omega_2$) to the shorter beam section $l_2$. The appearance of the natural frequencies $\omega_1$ and $\omega_2$ below and above and instead of only one natural frequency $\omega_0$ (equal length of both sections) causes a resonance curve A$\omega$, as indicated by the unbroken curve b in FIG. 3, with remarkably smaller amplitudes in the interesting frequency region $\omega_1$, $\omega_0$, $\omega_2$, therefore improving the shock resistance.

The natural frequency $\omega_0$ of the equal length sections is between the natural frequencies $\omega_1$ and $\omega_2$ of the two unequal length section since one of the equal length sections has a length between the two unequal length sections. The amplitude of the equal length section is higher since the natural frequency of each both sections is the same and therefore are additive or concentrated at a common frequency.

Appropriate variation of the dimensions of the oscilating beam can additionally improve the shock resistance. The usual dimensions of the prior art is a total beam length 1 of 12 mm, a beam width b of 4 mm and a beam thickness of 0.6 mm. Principally the following relations between the dimensions of the beam, the shock resistance, the sensitivity and the natural frequency of the oscillating system are valid: The shock resistance decreases proportional to the third power of the beam lenght 1. The sensitivity, on the other hand, increases proportional to the third power of the beam length 1.

The natural frequency ω decreases proportional to the second power of the beam length 1. This is represented by the experimentally establsihed curves of FIG. 4.

Figure 4:
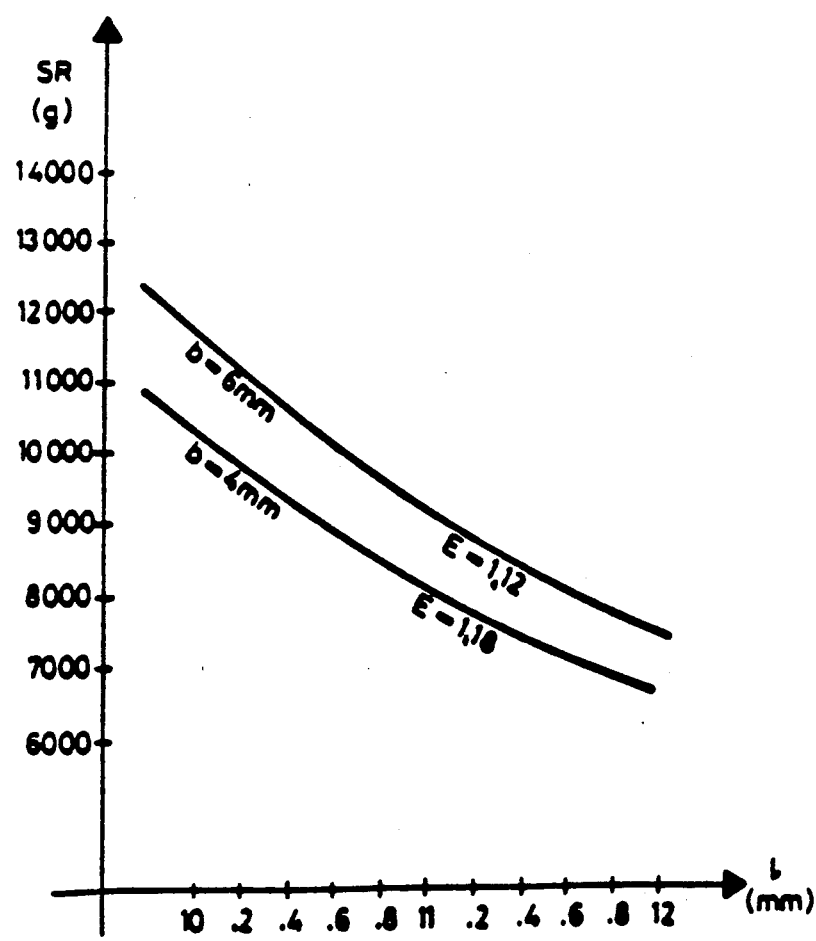
FIG. 4 is a graph of shock resistance as function of the beam length 1 the beam and the eccentricty E.

In FIG. 4 SR is the shock resistance, measured in g-units (acceleration due to gravity), 1 is the length of the beam, in mm., b is the width of the beam, and E is the eccentricity or ratio of the length of shorter beam segment $l_2$ to the length of the larger beam segment $l_1$. The number associated with g (vertical axis) signifies the deacceleration of an accelerometer dropping on the floor from 1 meter height. Experiments have demonstrated the probability of breakdown being in the order of 1% at a retardation or deacceleration of about 10,000 g. This value can be realized constructively. FIG. 4 shows the increase of the shock resistance by decreasing length 1 of the beam. Likewise, but to a smaller extent, the shock resistance can be increased by increasing the width b of the beam and decreasing the eccentricity E. On the other hand, the measuring sensitivity is decreasing with decreasing length 1 of the beam. This effect can only partially be compensated by increasing the charge amplifier gain, resulting in an increase of the amplifier noise and therefore threshold level.

Figure 5:
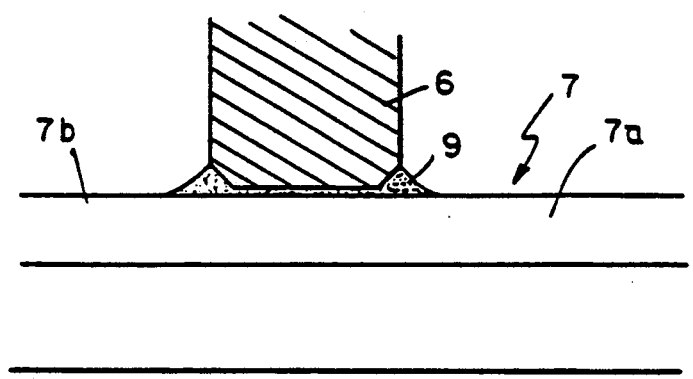
FIG. 5 is an enlarged section of the spacer and beam with bevelled gluing surfaces.
Figure 6:
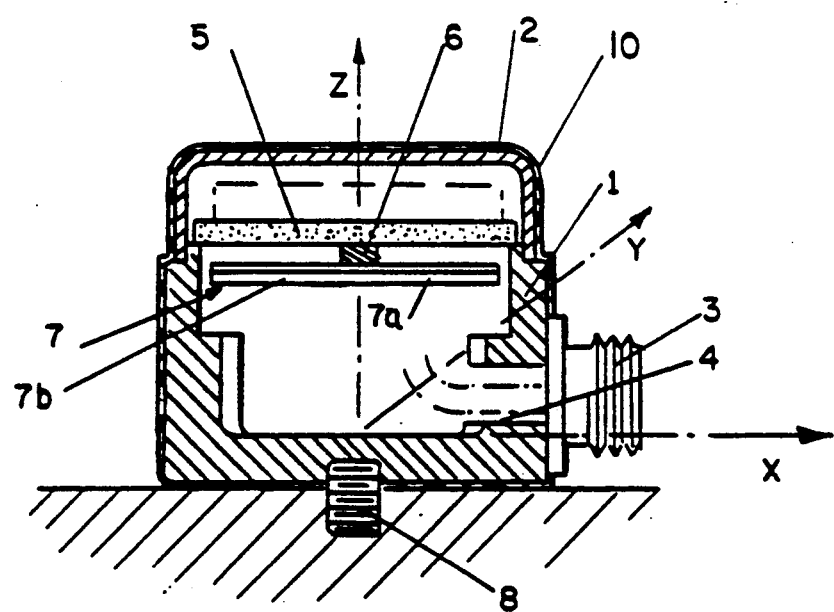
FIG. 6. is a cross-sectional view of an accelerometer with an elastic coating.

By taking experimental curves similar to those represented by FIG. 4 and taking into account the considerations made above, it is possible to get optimum dimensions of the beam. The total length of the beam has to be between 8 mm and 11 mm, the width between 2.5 mm and 6.5 mm, at a standard thickness of 0.6 mm. Reducing the length of the beam from the earlier 12 mm to the above indicated value raises also the natural frequency therefore allowing higher measuring frequencies. The quality of the fastening of the beam at the spacer is important for the shock resistance. If it is insufficient, the beam will easily break away from the spacer at shock influence. Experiments have shown Epoxy-Resins with silver or nickel additives being high-quality glues for this purpose. Bevelling the gluing surfaces as shown in FIG. 5 also improves the fastening. The glue is numeral 9. An elastic coating 10 covering the accelerometer housing 1 and cover 2 also improves its shock resistance as illustrated in FIG. 6.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. Accelerometer for the measurement of an axial acceleration, with a sensor part comprising:
   an electromechanical beam having two beam sections of unequal lengths;
   a beam carrier;
   a spacer connecting said beam and said beam carrier; and
   said beam being glued to the spacer, at bevelled gluing surfaces.

2. Accelerometer according to claim 1, wherein the eccentricity of the oscillating system, being the ratio of the length of the shorter beam section to that of the longer beam section is in the range of 1.02 and 1.20.

3. Accelerometer according to claim 2, wherein the total length of the beam is in the range of 8.0 mm to 11.0 mm and the width is in the range of 2.5 mm and 6.5 mm.

4. Accelerometer according to claim 1, including an elastic coating covering a housing and a cover, in which the beam, space and carrier beam are housed.

5. Accelerometer according to claim 1, wherein the total length of the beam is in the range of 8.0 mm to 11.0 mm and the width is in the range of 2.5 mm and 6.5 mm.

* * * * *